US00PP16222P3

(12) United States Plant Patent
Hofmann

(10) Patent No.: US PP16,222 P3
(45) Date of Patent: Jan. 31, 2006

(54) **NEW GUINEA *IMPATIENS* PLANT NAMED 'FISUPNIC MAPINK'**

(50) Latin Name: *Impatiens hawkeri*
Varietal Denomination: Fisupnic Mapink

(75) Inventor: Birgit C. Hofmann, Bendorf (DE)

(73) Assignee: Florfis AG, Binningen (SE)

( * ) Notice: Subject to any disclaimer, the term of this patent is extended or adjusted under 35 U.S.C. 154(b) by 133 days.

(21) Appl. No.: 10/829,221

(22) Filed: Apr. 22, 2004

(65) Prior Publication Data

US 2004/0216204 P1 Oct. 28, 2004

(30) Foreign Application Priority Data

Apr. 22, 2003 (CH) ..... 2003-1995

(51) Int. Cl.
*A01H 5/00* (2006.01)

(52) U.S. Cl. ..... Plt./318
(58) Field of Classification Search ..... Plt./318
See application file for complete search history.

(56) References Cited

U.S. PATENT DOCUMENTS

| | | | | | |
|---|---|---|---|---|---|
| PP10,858 | P | * | 4/1999 | Kientzler | Plt./318 |
| PP11,415 | P | * | 6/2000 | Trees | Plt./318 |
| PP13,096 | P2 | * | 10/2002 | Hofmann | Plt./318 |
| PP13,232 | P2 | * | 11/2002 | Hofmann | Plt./318 |
| PP13,579 | P2 | * | 2/2003 | Hofmann | Plt./318 |
| PP13,714 | P2 | * | 4/2003 | Hofmann | Plt./318 |
| PP14,833 | P2 | * | 5/2004 | Hofmann | Plt./318 |
| 2004/0216204 | P1 | * | 10/2004 | Hofmann | Plt./318 |

OTHER PUBLICATIONS

UPOV ROM GTITM Computer Database, GTI Jouve Retrieval Software 2004/06 Citations for 'Fisupnic Mapink'.*

* cited by examiner

*Primary Examiner*—Howard J. Locker
*Assistant Examiner*—W. C. Haas
(74) *Attorney, Agent, or Firm*—Foley & Lardner, LLP

(57) ABSTRACT

A new and distinct cultivar of New Guinea *Impatiens* plant named 'Fisupnic Mapink', particularly characterized by the combined features of light pink to nearly white, somewhat variable flower color; very large, round, flat flowers; medium green foliage; tall, and very well-branched, round plant habit; and about medium (mid season) flowering response.

1 Drawing Sheet

Botanical description: *Impatiens hawkeri.*
Variety denomination: 'Fisupnic Mapink'.

BACKGROUND OF THE INVENTION

The present invention comprises a new and distinct cultivar of New Guinea *Impatiens* plant, botanically known as *Impatiens hawkeri*, and hereinafter referred to by the cultivar name 'Fisupnic Mapink'.

'Fisupnic Mapink' is a product of a planned breeding program and originated from a hybridization made by the inventor, Birgit C. Hofmann, in a controlled breeding program in Hillscheid, Germany, in 2000.

The female parent was the variety 'Fisimp 131' (U.S. Plant Pat. No. 13,714), and characterized by round, rose-red flowers, medium green foliage, and about medium sized, round and tight plant habit.

The male parent of 'Fisupnic Mapink' was the variety 'Fisnics Light Pink' (U.S. Plant Pat. No. 13,579), having light pink flowers with a small purple eye, medium green foliage, small leaves, and medium sized, dense plant habit.

'Fisupnic Mapink' was discovered and selected as one flowering plant within the progeny of the stated cross by the inventor in April 2001 in a greenhouse in Galdar, Gran Canaria, Spain.

The first act of asexual reproduction of 'Fisupnic Mapink' was accomplished when vegetative cuttings were taken from the initial selection in July 2001 in a controlled environment in Galdar, Gran Canaria, Spain, by, or under the supervision of the inventor.

Horticultural examination of plants grown from these cuttings initiated in the spring of 2002 in Hillscheid, Germany, and continuing thereafter, has demonstrated that the combination of characteristics as herein disclosed for 'Fisupnic Mapink' are firmly fixed and are retained through successive generations of asexual reproduction. The new cultivar reproduces true to type.

'Fisupnic Mapink' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under green house conditions which approximate those generally used in commercial practice.

The following traits have been repeatedly observed and are determined to be basic characteristics of 'Fisupnic Mapink', which in combination distinguish this *impatiens* as a new and distinct cultivar:

1. light pink to nearly white, somewhat variable flower color;
2. very large, round, flat flowers;
3. medium green foliage;
4. tall, and very well-branched, round plant habit; and
5. about medium (mid season) flowering response.

Of the many commercial cultivars known to the inventor, the most similar in comparison to 'Fisupnic Mapink' is the parental variety 'Fisnics Light Pink' and the commercial variety 'Celebrette Appleblossom' (unpatented).

In comparison to 'Fisnics Light Pink', 'Fisupnic Mapink' has larger flowers, of basically similar, but more variable, flower color, with a less distinct purple eye. Additionally, 'Fisupnic Mapink' grows considerably taller.

In comparison to 'Celebrette Appleblossom', the flower color of 'Fisupnic Mapink' is a less deep pink. Furthermore, plants of 'Fisupnic Mapink' grow distinctly taller.

BRIEF DESCRIPTION OF THE DRAWING

The accompanying photographic drawing shows typical flower and foliage characteristics of 'Fisupnic Mapink' with colors being as true as possible with illustrations of this type. The photographic drawing shows a side view of a typical flowering plant of 'Fisupnic Mapink'.

DETAILED BOTANICAL DESCRIPTION

In the following description color references are made to The Royal Horticultural Society Colour Chart (R.H.S.). The color values were determined indoors from plants growing in a greenhouse in May 2003, in Hillscheid, Germany.

The description is based on plants which were planted as rooted cuttings in 12 cm pots in late February 2003, and then grown in the greenhouse at 16° C. minimum temperature. Most observations and measurements were made after the beginning of flowering in mid-May, when plants were about 12 weeks old.

PLANT

General appearance and form:

*Plant habit.*—Tall, round and very well-branched; growth is indeterminate, though relatively weak after beginning of flowering.

*Height.*—19.3 cm.

*Width.*—36.5 cm.

*Number of branches.*—14 to 15.

*Length of branches.*—19 to 22 cm.

*Internode length.*—5.5 to 7.0 cm.

*Diameter of branches.*—6 to 8 mm.

*Stem color.*—Mainly light green, RHS 145 A; a brownish hue, RHS 181 A, may occur at the nodes.

*Propagation.*—Terminal shoot tips for cuttings.

*Rooting.*—Roots initiate in about 18 days at 22° C., from sticking to transplanting.

*Cultivation time.*—It takes about 10 weeks of growing time to produce a marketable flowering plant in a 12 cm pot.

Foliage:

*Leaf arrangement.*—Primarily in whorls.

*Shape of leaf.*—Elliptic, with acute base and acuminate tip, surface glossy and somewhat rugose.

*Margin.*—Slightly serrated, ciliated.

*Leaf length.*—10.3 cm.

*Leaf width.*—4.0 cm on average.

*Upper surface main color.*—Medium green, uniform, mature leaves RHS 137 A, young leaves near RHS 139 B. Veins on upper surface: Brownish pink, RHS 47 C or lighter.

*Lower surface color.*—Light green, about RHS 139 C (both young and mature leaves).

*Petiole.*—1.5 to 2.5 cm in length, 3 mm in diameter; color upper side brownish pink, RHS 47 C, lower side, RHS 145 C.

INFLORESCENCE

*Flowering response.*—9.5 to 10 weeks after planting of rooted cuttings.

*Flowering season.*—Generally indeterminate, mainly from March to October, depending on light intensity.

Flower: Number of flowers per node 6 to 9, in various stages of development.

*Form of corolla.*—Single-type, 5 petals.

*Shape of corolla.*—Nearly round, with the petals overlapping, almost flat, large to very large.

*Size of corolla.*—Average length: 78 mm. Average width: 78 mm. Depth of corolla: 10 mm.

*Shape of petals.*—Cordate, slightly lobed at the top end, Top petal: 34 mm long, 53 mm wide. Lateral petals: 35 mm long, 40 to 42 mm wide. Lower petals: 37 mm long, 48 to 50 mm wide.

*Texture.*—Smooth, velvety.

*Aspect.*—Flat, parallel to the surface of the foliage canopy.

*Color (general tonality from a distance of three meters).*— Light pink, of somewhat variable intensity, may partly fade to nearly white.

*Ground color of upper surface.*—Light pink, from RHS 62 B to 62 C, no markings.

*Color of eye zone.*—Deep pink, RHS 66 C.

*Color of lower surface.*—RHS 62 C.

*Spur.*—Downwardly curved, 55 to 60 mm long; 3 mm in diameter at the flower end; color deep pink, RHS 53 D to 54 A.

*Peduncle color.*—Light green, RHS 145 C, upper end pink, RHS 54 B.

*Peduncle length.*—60 to 65 mm.

*Flower bud.*—Ovoid shape, 25 mm in length, 17 mm in diameter.

*Flower bud color.*—Between RHS 55 A and 55 B.

Reproductive organs:

*Stamens.*—5 in number, fused, upper surface color is mainly RHS N 57 C.

*Anthers.*—Fused, hooded.

*Pollen.*—Whitish-yellow, about RHS 8 D.

*Style and stigma.*—Five in number, very short, pale yellow, about RHS 150 D.

*Ovary.*—5-celled, 5 mm long, surface color green, RHS 139 B.

Disease/pest resistance/susceptibility: No observation made to date.

I claim:

1. A new and distinct cultivar of New Guinea *Impatiens* plant named 'Fisupnic Mapink' as described and illustrated herein.

* * * * *

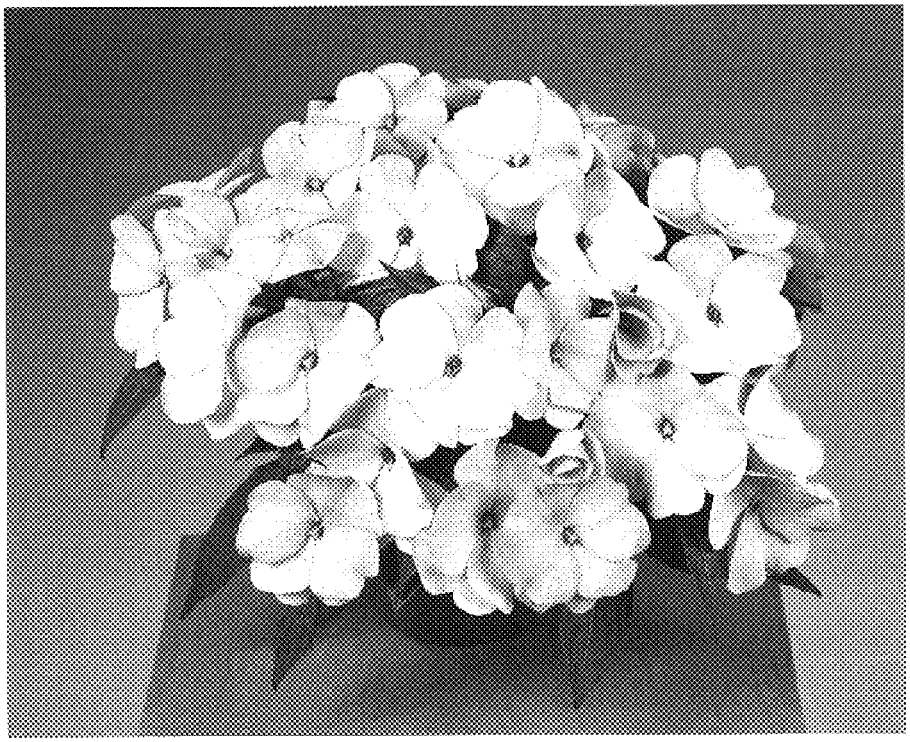

UNITED STATES PATENT AND TRADEMARK OFFICE

CERTIFICATE OF CORRECTION

PATENT NO. : PP 16,222 P3
DATED : January 31, 2006
INVENTOR(S) : Birgit C. Hofmann It is certified that error appears in the above-identified patent and that said Letters Patent is hereby corrected as shown below:

Title page,
Item [73], Assignee, should read:
-- Florfis AG, Binningen (CH) --.

Signed and Sealed this

Fourth Day of April, 2006

JON W. DUDAS
*Director of the United States Patent and Trademark Office*